United States Patent [19]

Bannick et al.

[11] Patent Number: 4,693,851

[45] Date of Patent: Sep. 15, 1987

[54] PURIFICATION OF ACID HALIDES

[75] Inventors: Mark A. Bannick, San Jose; George A. Divers, III, San Francisco; Viktors Jansons, Los Gatos, all of Calif.

[73] Assignee: Raychem Corporation, Menlo Park, Calif.

[21] Appl. No.: 834,703

[22] Filed: Feb. 28, 1986

Related U.S. Application Data

[63] Continuation-in-part of Ser. No. 721,525, Apr. 9, 1985.

[51] Int. Cl.$^4$ ............................................. C07C 51/64
[52] U.S. Cl. ........................... 260/544 D; 260/544 B; 260/544 P
[58] Field of Search ........... 260/544 D, 544 P, 544 B, 260/544 D

[56] References Cited

U.S. PATENT DOCUMENTS

| | | | |
|---|---|---|---|
| 4,136,113 | 1/1979 | Johnston et al. | 260/544 D |
| 4,374,770 | 2/1983 | Hyatt et al. | 260/544 D |
| 4,382,898 | 5/1983 | Rudolph et al. | 260/544 D |

FOREIGN PATENT DOCUMENTS

84/03891 10/1984 PCT Int'l Appl. .

OTHER PUBLICATIONS

Clark, N. G. et al., *Modern Organic Chemistry*, at p. 470, (1964), Oxford Univ. Press.

*Primary Examiner*—Paul J. Killos
*Assistant Examiner*—L. Hendriksen
*Attorney, Agent, or Firm*—Yuan Chao; Edith A. Rice; Herbert G. Burkard

[57] ABSTRACT

A method of purifying an aromatic carboxylic acid halide, for example p-phenoxybenzoyl chloride, comprising the steps of: (a) adding an acidic catalyst, for example a molecular sieve, to the acid halide; (b) heating the resulting mixture of the acidic catalyst and the acid halide to a temperature of about 180° C. to about 250° C. for a period of at least 0.5 hours; (c) distilling the mixture to obtain acid halide substantially free of aldehyde and the halo derivative thereof. Optionally, a reactive aromatic compound may be added to the mixture of the acid halide and the acidic catalyst before the heating step. The process is particularly useful for providing aromatic acid halides of sufficient purity for preparing melt stable aromatic polyketones.

11 Claims, No Drawings

PURIFICATION OF ACID HALIDES

This is a continuation-in-part of application Ser. No. 721,525, filed Apr. 9, 1985, the disclosure of which is hereby incorporated by reference.

BACKGROUND OF THE INVENTION

This invention relates to the purification of acid halides.

In the production of an acid halide, the corresponding aldehyde is generally present as a by-product. For certain uses of the acid halide the aldehyde impurity must be reduced to extremely low levels. This is particularly true in the case of aromatic acid halides when used to prepare aromatic polyketones. Even small amounts of aldehyde present in the monomer can lead to melt instability of the polymer. For example p-phenoxybenzoyl halides, in particular the chloride, are useful in the production of poly(aryl ether ketones) comprising the repeat unit

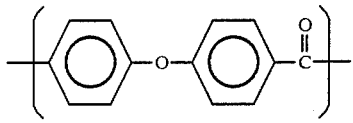

It has been found that in preparing polymers containing this repeat unit from p-phenoxybenzoyl chloride (or other halide), very small amounts of p-phenoxybenzaldehyde or p-phenoxybenzal chloride present as an impurity results in a polymer which tends to be melt unstable, that is, tends to decompose and/or crosslink in the melt, and is therefore not suitable for use for fabrication into articles, coatings, etc. by melt processing techniques.

In the preparation of p-phenoxybenzoic acid, p-phenoxybenzaldehyde is generally present as an undesirable impurity in the product. (Similarly, where other acid halides or dihalides are used, the corresponding aldehydes may be present as undesirable impurities.) If p-phenoxybenzoic acid is converted to p-phenoxybenzoyl chloride, p-phenoxybenzaldehyde and/or its chlorinated derivative, p-phenoxybenzal chloride is present in the product. The content of p-phenoxybenzaldehyde can be reduced by converting it to p-phenoxytoluene which can be removed from p-phenoxybenzoic acid by crystallization. This is done as a separate purification step by reacting the impure p-phenoxybenzoic acid with hydrogen in the presence of a Group VIII metal catalyst or a noble metal catalyst. Such processes are described in U.S. Pat. No. 3,584,039 to D. H. Meyer and U.S. Pat. No. 3,456,001 to G. P. Olsen. Following removal of the p-phenoxytoluene the p-phenoxybenzoic acid is converted to p-phenoxybenzoyl chloride and then distilled. The p-phenoxybenzaldehyde and p-phenoxybenzal chloride cannot be removed in the distillation step as they co-distill with p-phenoxybenzoyl chloride. Thus the separate step of converting it to p-phenoxytoluene has been required by the prior art.

We have now discovered a process by which, for example, p-phenoxybenzaldehyde can be removed from impure p-phenoxybenzoyl chloride during distillation or prior to distillation, preferably in the distillation vessel. The term p-phenoxybenzaldehyde is used herein to refer to the compound per se and its chloro derivative present in the impure p-phenoxybenzoyl chloride.

SUMMARY OF THE INVENTION

This invention provides a method of purifying an aromatic carboxylic acid halide comprising the steps of:
(a) adding an acidic catalyst to the acid halide;
(b) heating the resulting mixture of the acidic catalyst and the acid halide to a temperature of about 180° C. to about 250° C. for a period of at least 0.5 hours;
(c) distilling the mixture to obtain acid halide substantially fre of aldehyde and the halo derivative thereof.

The acid halide is preferably p-phenoxybenzoyl chloride or diphenyl ether-4,4'-dicarbonyl dichloride. The acidic catalyst is preferably a molecular sieve. A reactive aromatic compound may be added to the mixture of the acid halide and the acidic catalyst before the heating step.

DETAILED DESCRIPTION OF THE INVENTION

The acid halide purified in accordance with this invention is preferably an aromatic acid halide. The process is particularly advantageous for purifying aromatic acid halides to be used in the preparation of aromatic polyketones. Such polyketones can be produced by the reaction of an acid halide such as p-phenoxybenzoyl chloride, phenoxyphenoxybenzoyl chloride or the like or by reacting a diacid dihalide with a suitable comonomer, for example diphenyl ether-4,4'-dicarbonyl chloride iso- or terephthaloyl chloride with diphenyl ether, diphenoxybenzene, 4-phenoxybiphenyl. A description of producing aromatic polyketones from acid halide monomers can be found in published patent application WO 84/03891, the disclosure of which is incorporated herein by reference.

The purification of p-phenoxybenzoyl halide and diphenyl ether-4,4'-dicarbonyl dichloride are of particular interest and the invention will be described in detail with regard to these compounds. It is to be understood that the invention is not limited to purification of the above-mentioned halides but encompasses the purification of acid halides in general.

The acidic catalyst is added to the p-phenoxybenzoyl halide to be purified in an amount of about 0.001 to about 10%, preferably of about 0.5 to about 4% by weight. The acidic catalyst can be, for example, a molecular sieve, sulfuric acid or the like. The use of molecular sieves is preferred.

The term molecular sieve is used herein to mean a crystalline inorganic material having a plurality of microscopic interconnecting voids or channels extending therethrough. Such materials include crystalline aluminosilicates, silicoaluminophosphates, and aluminophosphates in acid form or as a salt with a group IA or group IIA element such as sodium, potassium, magnesium or calcium and silica polymorphs. Preferred molecular sieves for use in this invention are sodium aluminosilicates. Molecular sieves contain acidic sites under anhydrous conditions and the sieves may be further activated in the presence of acid chlorides. The molecular sieve is added to the acid halide in particulate form. Preferably the particle size is from about 1 micron to about 10 millimeters, most preferably from about 1 to about 200 microns.

The resulting mixture of acid halide and acidic stabilizer may be heated to elevated temperatures, for example about 120° C. to about 300° C., preferably about 180° C. to about 250° C. and most preferably about 200° C. to about 220° C. The mixture should be maintained at this temperature for at least about 0.5 hours. Generally the mixture is maintained at this temperature for about 0.5 to about 72 hours, preferably from about 0.5 to about 50 hours and most preferably from about 0.5 to about 24 hours.

While not wishing to be bound by any theory, it is believed that treatment with the acidic catalyst prior to distillation causes the aldehyde to react with the acid halide to produce a relatively high molecular weight derivative. On distillation the derivative does not co-distill with the acid halide, thus yielding a product with low aldehyde content. For p-phenoxybenzoyl chloride, it is believed that reaction takes place between the aldehyde group and an aromatic hydrogen reactive towards electrophilic substitution in the phenoxy group.

We have further found that the addition of a reactive aromatic compound of higher reactivity than the acid halide, for example acenaphthene or carbazole or their polymers or derivatives or even another aromatic acid halide having a reactive aromatic hydrogen, can insure that high boiling derivatives of the aldehyde are formed within the reaction period. Addition of a reactive aromatic compound is generally desirable if the acid halide is a diacid halide lacking an electrophilically reactive aromatic hydrogen. For example, a carbazole compound or even p-phenoxybenzoyl chloride itself can function as a reactive aromatic compound for the purification of diphenyl ether-4,4'-dicarbonyl dichloride. Those skilled in the art will recognize that, in selecting the reactive aromatic compound, it distillation characteristics should be such that it will not co-distill with the acid halide being purified.

Following the addition of the acidic catalyst and the heat treatment step, the acid halide mixture is distilled, preferably in vacuo, under conventional distillation conditions. A polymerization inhibitor such as triphenyl phosphine oxide can be added to the mixture if desired.

The degree of purity required for polymerization grade acid halide is such that even amounts of the aldehyde too low to be detected by gas chomatography can adversely affect the polymer stability. In order to detect such small amounts of impurity, it has been found that an absorbancy index test, as described more fully below, is useful. Where the acid halide is p-phenoxyl benzoyl chloride, it preferably has a p-phenoxybenzaldehyde content of less than about 0.2%, more preferably less than about 0.050, and in particular less than about 0.002.

The following examples illustrate the method of this invention.

EXAMPLE 1

The following reagents are charged directly into a 22 L (liter) flask of a glass vacuum distillation apparatus: 20 kg of p-phenoxybenzoyl chloride; 100 g of triphenylphosphine oxide; and 200–600 g of dried molecular sieves, Aldrich, 3 or 4 Angstrom, 8-12 mesh. (The molecular sieves are dried by heating at 300°–400° C. for 5 hours.) The mixture is heated, preferably with vigorous stirring, under a positive pressure of nitrogen at 200°–220° C. for 16-24 hours. The viscous brown mixture is tested for the presence of p-phenoxybenzaldehyde and its derivatives with the acenaphthene test (see below). If this test is negative, distillation is carried out. If the test is positive, the mixture must be heated under the above conditions until the acenaphthene test is negative.

The heating mantle for the distillation pot is set at 232° C. The vacuum pump is turned on and the pressure of the system is checked so that it is below 10 mm Hg (temperature of vapor at distillation head about 160° C.). The vacuum pump is protected by three traps immersed in liquid nitrogen. The column, 3 inches in diameter and 3 feet in length, is packed with interlocking ceramic saddles and provides approximately 10 theoretical plates.

The forecut of about 1 kg is taken at a reflux ratio of 10:1. The main fraction is collected at a rapid distillation rate. When the vapor no longer reaches the head of the column the distillation is considered finished. Collection of a final fraction is necessary only if the original p-phenoxybenzoyl chloride contained significant amounts of impurities other than p-phenoxybenzaldehyde and its derivatives. The clear, colorless distillate is transferred to clean 500 ml Wheaton glass bottles or 1 gal amber bottles which have been dried in an oven at 110° C. for 1 hour and cooled in a dessicator. The bottles are blanketed with dry nitrogen, capped with polyethylene-lined caps, sealed with Parafilm and stored at room temperature.

The distillation produces about 15-17 kg of main fraction plus about 1 kg of recyclable forecut for a total yield of about 80-90%.

EXAMPLE 2

Acenaphthene Test

In a small vial, about 200 mg (12 drops) of crude p-phenoxybenzoyl chloride is dissolved in about 2 ml of trifluoroacetic acid. To this yellowish-brown solution is added three drops of 5 wt % acenaphthene/dichloromethane solution. The vial is swirled to mix the contents thoroughly and the color is immediately observed.

NEGATIVE TEST: The color of the solution is yellowish-brown, indicating that no p-phenoxybenzaldehyde or its derivatives are present.

POSITIVE TEST: The color of the solution is green or blue-green, indicating that p-phenoxybenzaldehyde or its derivatives are still present.

EXAMPLE 3

This procedure describes the absorbancy index (As) test used to determine the aldehyde content of acid chlorides. Chemically, it is based on the conversion, in the presence of concentrated sulfuric acid and of acid halide, of the aldehyde or its derivatives to a colored species which can be detected spectrophotometrically.

Where the acid chloride is a liquid, for example, p-phenoxybenzoyl chloride, concentrated sulfuric acid (5.00 mL, clear and colorless) is pipetted into a snap cap vial with a bottom diameter of 3 cm. The vial is capped, and it and its contents are weighed. The cap is removed and acid halide (2 drops, ca. 30 mg) is floated on top of the sulfuric acid. The vial is recapped and reweighed, taking care to disturb the contents as little as possible. After letting the vial stand undisturbed for 3-5 min, it is swirled so as to mix its contents thoroughly. The cap is removed and the vial is allowed to stand in a fume hood for at least 2 min to allow hydrochloric acid to escape.

The visible absorption spectrum of the resulting solution is recorded, using concentrated sulfuric acid as the reference solution and setting the baseline at 800 nm as zero. If the absorbance at 508 nm is less than 0.05 absorbance units, the above procedure is repeated using 6 drops of acid halide to obtain more accurate readings.

The absorbancy index As is calculated from the formula $$As = A/bc$$

where A is the absorbance at 508 nm, b is the path length in cm, and c is the concentration of acid halide in sulfuric acid, in g/mL. As is linearly related to the concentration of aldehyde in the acid chloride.

Where the acid chloride is a solid, for example, diphenyl ether -4,4'-dicarboxyl dichloride, the solution preparation procedure is modified as follows: into a snap cap vial are weighed, accurate to the nearest 0.001 g, the solid acid chloride (about 0.5 g) and a liquid acid chloride, for example, p-phenoxybenzoyl chloride about 1.0 g, known As). The vial is capped acid and its contents are heated to 170° C. until complete dissolution occurs, about 5 minutes. This solution should be used immediately upon removal from the heat, before any precipitation upon cooling. The sulfuric acid treatment and As measurement are performed as aforementioned, except that in the calculations, the As attributable to liquid acid chloride is substrated to arrive at the As of the solid acid chloride.

EXAMPLE 4

Diphenyl ether-4,4'-dicarbonyl dichloride was prepared from diphenyl ether-4,4'-dicarboxylic acid (200 g) by treatment with thionyl chloride (400 g) and N,N-dimethylforamide (8 g) at 90° to 100° C. for 2 hr in a flask equipped with a condenser and a drying tube. After removing the excess thionyl chloride by vacuum stripping, the diacid dichloride was obtained as a yellow-brown solid. This material had an As of 1013.

EXAMPLE 5

The diphenyl ether-4,4'-dicarbonyl dichloride of example 4 was distilled after various treatments. The absorbancy index As was then measured for each sample. Results are provided in Table I.

TABLE I

| Treatment | Time (hrs) | Temp (°C.) | Absorbancy Index (As) |
| --- | --- | --- | --- |
| Distilled without treatment | — | — | 1285 |

TABLE I-continued

| Treatment | Time (hrs) | Temp (°C.) | Absorbancy Index (As) |
| --- | --- | --- | --- |
| 2 wt % MS* | 80 | 200-210 | 9 |
| 2 wt % MS plus 2 wt % p-phenoxybenzoyl chloride | 16 | 200-210 | 882 |
| 4 wt % MS plus 4 wt % vinyl carbazole | 60 | 200-210 | 16 |

*MS = 3 A molecular sieves, dried 5 hr at 300-350 C.

We claim:

1. A method of purifying an aromatic carboxylic acid halide comprising the steps of
   (a) adding a acidic molecular sieve catalyst which is a crystalline aluminosilicate, silicoaluminophosphate, or aluminophosphate in acid form or a salt with a group IA or group IIA element, or a silica polymorph, in an amount between about 0.001 to about 10% by weight to said aromatic carboxylic acid halide;
   (b) heating the resulting mixture of said acidic catalyst and said acid halide to a temperature of about 180° C. to about 250° C. for a period of at least of 0.5 hrs;
   (c) distilling the mixture to obtain acid halide substantially free of aldehyde and the halo derivative thereof.

2. A method according to claim 1 further comprising the step of adding a reactive aromatic compound which is acenaphthene or carbazole or a polymer or derivative thereof to the mixture before said heating step.

3. A method according to claim 1 wherein said acidic molecular sieve catalyst is a crystalline aluminosilicate.

4. A method according to claim 1 wherein said acidic molecular sieve catalyst is a sodium aluminosilicate.

5. A method according to claim 1 wherein said acid halide is p-phenoxybenzoyl halide.

6. A method according to claim 1 wherein said acid halide is p-phenoxybenzoyl chloride.

7. A method according to claims 1 or 2 wherein said acid halide is diphenyl ether-4,4'-dicarbonyl dihalide.

8. A method according to claims 1 or 2 wherein said acid halide is diphenyl ether-4,4'-dicarbonyl dichloride.

9. A method according to claim 4 wherein said acid halide is p-phenoxybenzoyl chloride.

10. A method according to claim 4 wherein said acid halide is diphenyl ether-4,4'-dicarbonyl dichloride.

11. A method according to claim 1 further comprising the step of adding triphenylphosphine oxide to the mixture before said heating step.

* * * * *